(12) United States Patent
Hall et al.

(10) Patent No.: US 7,804,598 B2
(45) Date of Patent: Sep. 28, 2010

(54) HIGH POWER ACOUSTIC RESONATOR WITH INTEGRATED OPTICAL INTERFACIAL ELEMENTS

(75) Inventors: Clive E. Hall, Ashford (GB); Li Jiang, Ridgefield, CT (US); Timothy G. J. Jones, Cottenham (GB); Gary J. Tustin, Sawston (GB)

(73) Assignee: Schlumberger Technology Corportion, Ridgefield, CT (US)

( * ) Notice: Subject to any disclaimer, the term of this patent is extended or adjusted under 35 U.S.C. 154(b) by 1090 days.

(21) Appl. No.: 11/499,329

(22) Filed: Aug. 4, 2006

(65) Prior Publication Data

US 2008/0030714 A1 Feb. 7, 2008

(51) Int. Cl.
*G01N 21/55* (2006.01)
(52) U.S. Cl. ..................................................... 356/445
(58) Field of Classification Search ................. 356/445, 356/480
See application file for complete search history.

(56) References Cited

U.S. PATENT DOCUMENTS

| | | | |
|---|---|---|---|
| 4,216,671 A | | 8/1980 | Kurland |
| 4,956,149 A | | 9/1990 | Kawana et al. |
| 5,159,411 A | * | 10/1992 | Hammerich et al. ......... 356/432 |
| 5,339,674 A | * | 8/1994 | Hammerich et al. ....... 73/24.02 |
| 5,348,002 A | * | 9/1994 | Caro .......................... 600/310 |
| 5,889,209 A | | 3/1999 | Piedrahita et al. |
| 6,426,974 B2 | | 7/2002 | Takahashi et al. |
| 6,437,326 B1 | | 8/2002 | Yamate et al. |
| 6,627,873 B2 | | 9/2003 | Tchakarov et al. |
| 6,880,402 B1 | | 4/2005 | Couet et al. |
| 6,886,406 B1 | | 5/2005 | Couet et al. |
| 6,995,360 B2 | | 2/2006 | Jones et al. |
| 7,710,566 B2 | * | 5/2010 | Arnott et al. ................. 356/432 |

FOREIGN PATENT DOCUMENTS

| | | |
|---|---|---|
| EP | 1070953 A1 | 1/2001 |
| GB | 2 269 674 B | 10/1995 |
| GB | 2 336 668 B | 2/2003 |

(Continued)

OTHER PUBLICATIONS

Compton et al 'Electrode processes at the surface of sonotrodes' Electrochimica Acta, vol. 41, No. 2, 1996, pp. 315-320.

(Continued)

*Primary Examiner*—Roy Punnoose
(74) *Attorney, Agent, or Firm*—James McAleenan; Vincent Loccisano; Brigid Laffey

(57) ABSTRACT

Embodiments of the present invention provide methods and systems for integrating optical interfacial elements with a high power acoustic resonator. More specifically, but not by way of limitation, in certain embodiments of the present invention, one or more optical interfacial elements may be integrated with a high power acoustic resonator to provide a robust sensing device that may provide for acoustic cleaning of the optical interfacial elements and/or combining optical and acoustic measurements made by the integrated system for analysis purposes. In certain aspects, the high power acoustic resonator may include an acoustic horn for focusing acoustic energy and the optical interfacial elements may be integrated with the acoustic horn.

30 Claims, 11 Drawing Sheets

FOREIGN PATENT DOCUMENTS

| | | | |
|---|---|---|---|
| GB | 2 369 679 B | 4/2004 |
| GB | 2 369 680 B | 4/2004 |
| GB | 2 379 976 B | 2/2005 |
| WO | 2004/003506 A2 | 1/2004 |
| WO | 2004/003506 A3 | 1/2004 |

OTHER PUBLICATIONS

Durant et al 'Sonoelectrochemistry: the effects of ultrasound on organic electrochemical reduction' Electrochimica Acta, vol. 41, No. 2, 1996, pp. 277-284.

Reisse et al 'Sonoelectrochemistry in aqueous electrolyte: a new type of sonoelectroreactor' Electrochimica Acta, vol. 39, No. 1, 1994, pp. 37-39.

Simm et al 'Sonically assisted electroanalytical detection of ultratrace arsenic' Analytical Chemistry, vol. 76, 2004, pp. 5051-5055.

Windsor Scientific, "Sonotrode", Print out from Product Information, www.windsorscientific.co.uk/DesktopDefault.aspx?tabindex=65&tabid=65 (Aug. 17, 2006).

Bublitz et al: "Adaptation of approved laser-induced time-resolved fluorescence spectroscopy in offshore applications: Experience of 24 months measurements in produced water", allegedly presented at the 7th Oil-in-Water Monitoring Workshop, Nov. 23-24, 2005. Section 3.2 on pp. 9-12 has been alleged to be relevant. Place where presented not given but may be Aberdeen, United Kingdom.

European Patent Office, Communication Pursant to Rule 114(2) EPC, dated Jun. 16, 2010, 8 pages.

* cited by examiner

HIGH POWER ACOUSTIC RESONATOR WITH INTEGRATED OPTICAL INTERFACIAL ELEMENTS

CROSS-REFERENCE TO RELATED APPLICATIONS

This application is related to U.S. application Ser. No. 11/499,332, now U.S. Pat. No. 7,710,000 B2, filed on a date even herewith by Clive E. Hall et al. and entitled "An Erosion And Wear Resistant Sonoelectrochemical Probe", the disclosure of which is incorporated herein by reference for all purposes. This application is ALSO related to the following commonly-owned patents, U.S. Pat. No. 6,880,402 ("the '402 patent) to Couet et al., U.S. Pat. No. 6,886,406 ("the '406 patent) to Couet et al., and U.S. Pat. No. 6,995,360 ("the '360 patent") of which the entire disclosure of each is hereby incorporated by reference for all purposes.

BACKGROUND OF THE INVENTION

Cleaning methods have been proposed in the art for maintaining the operation of optical windows and/or sensing membranes in remote and/or fouling environments. For example, the patent application Ser. No. GB 2379976 to Benson describes an optical cell in which the outer part of the optical window that is in contact with a material being analyzed may be rotated and passed over a wiper. Benson further provides that a cleaning fluid can be used with the optical window to aid the removal of contaminants from the portion of the window rotated for cleaning and warm air may be used to dry the window prior to it being rotated back into its original position. Similarly, U.S. Pat. No. 6,627,873 to Tchakarov et al. describes the use of wiper blades to maintain the transmission properties of optical windows used to measure the concentration of carbon dioxide in fluids produced from subsurface formations by means of an infrared gas sensor.

With regard to acoustic sensors and/or acoustic resonators, the use of acoustic devices to measure organic and inorganic deposits associated with wellbores for producing hydrocarbons is described in the commonly owned '402 and '406 patents. Additionally, these two patents disclose using such acoustic devices in proximity to optical sensors to provide for cleaning the optical sensors and/or using spectroscopic-type measurements from the optical sensors in combination with the acoustic-type measurements from the acoustic devices to measure properties of deposits associated with the hydrocarbon production.

Furthermore, the commonly owned '360 patent describes embedding a diode and a detector of a mid-infrared gas sensor in separate acoustic devices that are located down a borehole—the diode and detector being used to measure properties of a gas located between the diode and the detector—and using the acoustic devices to provide for acoustic cleaning of the diode and the detector. Additionally, the GB 2336668 patent to Byatt et al. discloses the use of fluorescence spectroscopy to determine the concentration of oil in water and mentions that fouling of the optical windows might be prevented or minimized by the use of oil-repellent coatings, turbulent flow or application of ultrasound.

U.S. Pat. No. 6,437,326 to Yamate and Mullins may be understood to suggest the use of ultrasonic oscillators to clean optical windows in optical sensors placed permanently in wells producing hydrocarbons. U.S. Pat. No. 6,426,974 discloses the application of high frequency ultrasound to the cleaning of a flow cell that is designed for use in a light scattering apparatus. The WO2004/003506 application to Pope et al. provides for an optical sensor to measure the concentration of methane gas that can be produced from coal beds, wherein an acoustic cleaner, that is separate from an optical window, may be used to ultrasonically clean the optical window. Likewise, U.S. Pat. No. 4,216,671 to Kurland discloses the use of transducers to clean sensor membranes that are separate from the transducers. Furthermore, Windsor Scientific Ltd in the United Kingdom manufacture what is known as a sonotrode, which is a carbon electrode that is attached by glass rods to an acoustic resonator.

U.S. Pat. No. 4,956,149 to Kawana and Ito describes a biosensor combined with a piezoelectric actuator to dispense liquid drops with highly reproducible volumes. GB2269674 to Campbell discloses an electrochemical membrane sensor containing a piezoelectric transducer for the purposes of cleaning the membrane and the attached electrode and of mixing the electrolyte contained in the sensor. In addition, U.S. Pat. No. 5,889,209 to Piedrahita and Wong discloses the use of ultrasound from an ultrasonic transducer to clean a sensor's membrane, wherein the ultrasonic transducer and the sensor are placed adjacent to each other.

BRIEF SUMMARY OF THE INVENTION

Embodiments of the present invention relate to integrating an optical interfacial element and an optical system with a high power acoustic resonator. By way of example, but not by way of limitation, the optical interfacial element may comprise an optical window, an optical lens, an optical prism or the like. By further way of example, but not by way of limitation, the optical system may comprise of one or more of optical light pipes, optical fibers and optical mirrors. More specifically, but not by way of limitation, the high power acoustic resonator may be used to generate acoustic energy that may be used to clean one or more of the integrated optical interfacial elements and/or may be used to generate a harmonic frequency for analyzing a substance in contact with one or more elements of the high power acoustic resonator with integrated optical interfacial elements and optical system.

In some embodiments of the present invention, the high power acoustic resonator may comprise an acoustic body with a base end and a peripheral end, wherein the peripheral end defines a surface with an aperture in the surface. In such embodiments, an optical interfacial element and an optical system configured to provide an optical path through the acoustic body to and from the aperture of the optical element containing the optical interfacial element may be integrated with the acoustic body, and acoustic energy generated by the high power acoustic resonator may be transmitted to the optical interfacial element. In certain aspects of embodiments of the present invention, the acoustic body is an acoustic horn. Additionally, by integrating the optical element with the acoustic resonator, it may be possible to produce a rugged optical interface for use in harsh conditions that may optimize acoustic cleaning effects and/or provide for combined opto-acoustic sensing.

In certain embodiments of the present invention, the optical element may comprise a prism. In such embodiments, the optical element may be configured to provide for reflection from a total internal reflecting surface formed at one or more surfaces of the optical interfacial element. Merely by way of example, the optical element may comprise a long thin rectangular prism and electromagnetic radiation may be reflected down the optical element to provide for multiple interactions with a substance in contact with the optical element.

In certain aspects of embodiments of the present invention, the optical system may comprise one or more optical fibers, light pipes (described further as optical conduits) or optical lenses and the optical system may be disposed within the acoustic horn. Steerable mirrors may be used in conjunction with the optical conduits to provide for directing electromagnetic radiation beams at varying angles onto surfaces of the optical element. Merely by way of example, one or more steerable mirrors may provide that a beam of electromagnetic radiation is directed onto a surface of the optical element such that total internal reflection of the electromagnetic radiation beam occurs within the optical element.

The optical element may comprise natural diamond, synthetic diamond, sapphire, silica, silicon, germanium, zinc selenide, zinc sulphide, barium fluoride, calcium fluoride, yttrium oxide or the like. In certain aspects, the electromagnetic radiation utilized may comprise infrared radiation. Further, in some aspects, the electromagnetic radiation transmitted to the optical interfacial element by the optical system and passing through the optical interfacial element may be measured to determine the composition of material located beyond the optical interfacial element. Yet further, in some aspects of the present invention, the acoustic resonator may be configured to provide fundamental resonant frequencies in the range of 10-250 kHz. Moreover, in some embodiments, a processor may be configured with the acoustic resonator and integral optical element to provide for controlling the device and processing optical and/or acoustic measurements determined by the device.

In one embodiment, the high power acoustic resonator may operate in a longitudinal mode. In such an embodiment, the surface formed by the second end of the acoustic body and/or the interface surface of the optical element may move predominantly normal rather than parallel to the exposed surface.

Further areas of applicability of the present invention will become apparent from the detailed description provided hereinafter. It should be understood that the detailed description and specific examples, while indicating various embodiments of the invention, are intended for purposes of illustration only and are not intended to limit the scope of the invention.

BRIEF DESCRIPTION OF THE DRAWINGS

The present invention will become more fully understood from the detailed description and the following drawings.

Figure 1:
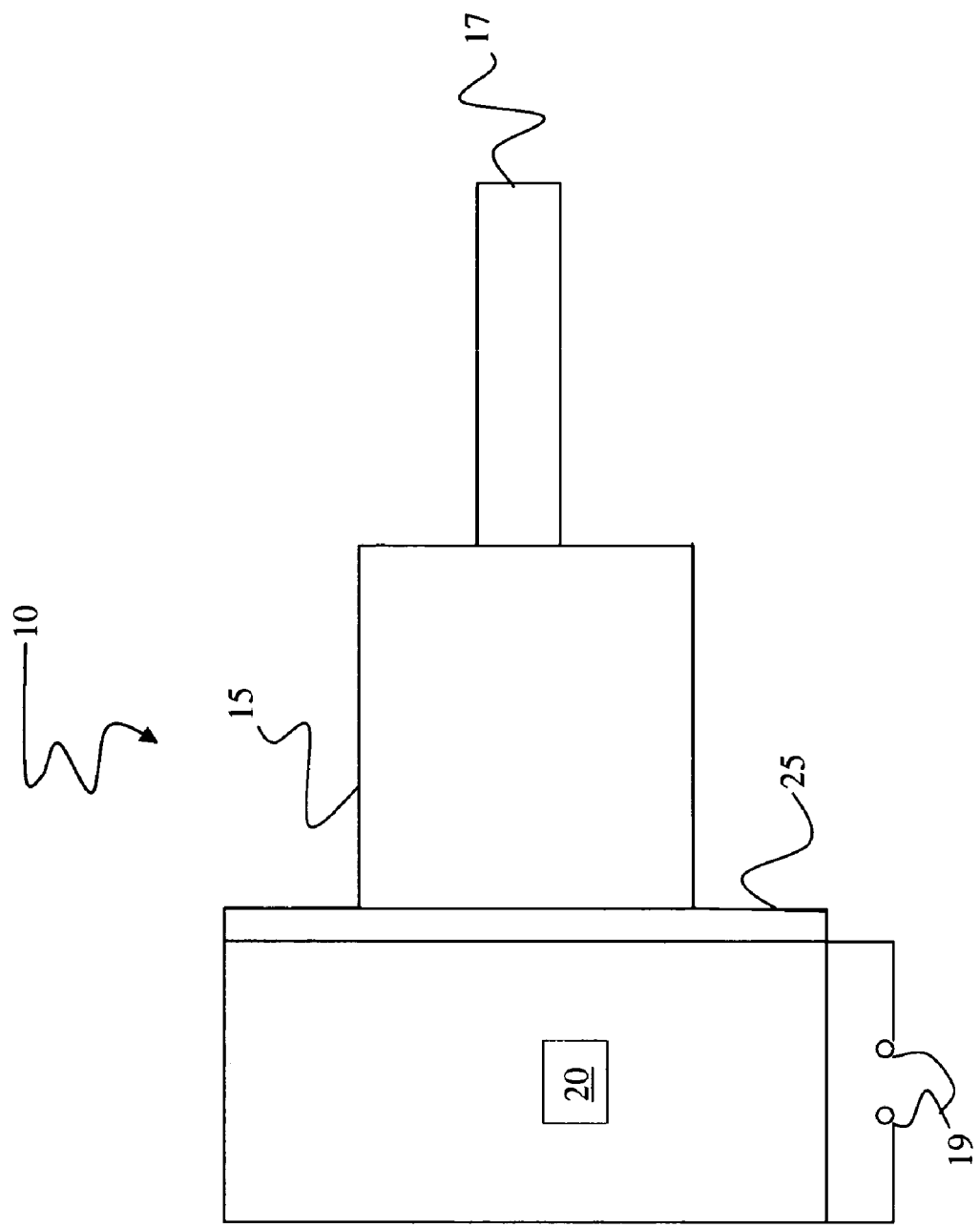
FIG. 1 is a schematic type illustration of a high power acoustic resonator that may be used in an embodiment of the present invention.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The following description of various embodiments of the present invention is merely exemplary in nature and is in no way intended to limit the invention, its application, or uses.

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments maybe practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

In a high power acoustic resonator, an acoustic horn may be used to generate high power ultrasound. The high power acoustic resonator may comprise an acoustic or ultrasonic (the words may be used interchangeably herein) body that may be referred to as an acoustic horn that is a mechanical device for transmitting and often amplifying the displacement and a means of generating a sinusoidal displacement—such as a piezoelectric or magnetostrictive elements. The amplification of the displacement is achieved by the reduction in cross-sectional area along the length of the horn, which is typically made of a metal such as steel or titanium.

FIG. 1 shows a schematic of a high power acoustic resonator that may be used in an embodiment of the present invention. Generally, a high power acoustic resonator 10 may comprise an acoustic body/acoustic horn 15 (the terms acoustic body and acoustic horn may be used interchangeably herein) attached to an ultrasonic transducer 20. A power source 19 may be coupled with the ultrasonic transducer 20 to provide power to the ultrasonic transducer 20. In an embodiment of the present invention, a high power acoustic resonator with an integrated optical element and optical system may consist of an ultrasonic piezoelectric transducer coupled to a suitable metal horn.

In one aspect of such an embodiment, the piezoelectric transducer may be configured to operate in a longitudinal mode. In such an aspect, the resulting ultrasonic device may be characterized by having a sharp resonant frequency, which can be conveniently determined by the measurement of the admittance (or impedance) spectrum of the device. Furthermore, the resonance frequency of the appropriate longitudinal mode of such a device is sensitive to any material deposit that forms on the tip of the horn and the magnitude of the frequency shift is a measure of the mass loading. The high power acoustic resonator 10 may comprise an ultrasonic piezoelectric transducer coupled to a suitable metal horn and may operate in the frequency range 10-250 kHz and may deliver high levels of acoustic power, typically in the range 1-500 W, when driven by a high input alternating voltage at its resonant frequency.

The resonant frequency of the acoustic device operating in a longitudinal mode is determined by the thickness of the piezoelectric and the materials from which the piezoelectric and acoustic horn 15 are constructed. The acoustic horn 15 may have a stepwise tapering design, an exponentially reducing diameter or the like. In some acoustic horn 15 designs, the tapering is degenerated to a single step giving the acoustic horn 15 a pin-like shape. Other horn shapes can be envisaged, including the case where its thickness is very much less than the wavelength of sound and the horn is a thin layer of material that couples the ultrasonic transducer to the material with which it is in contact.

Acoustic horns are well known devices for generating high power ultrasound most commonly in the frequency range 20-100 kHz. An acoustic (or ultrasonic) horn may consist of a means of generating a sinusoidal displacement, such as a piezoelectric or magnetostrictive element, and a mechanical device for transmitting and frequently amplifying the displacement. The displacement of the acoustic horn may be generated by several piezoelectric elements and the amplification of the displacement is achieved by the reduction in cross-sectional area along the length of the horn, which is typically made of a metal such as steel or titanium. The horn may be designed such that an antinode is located at the tip of the horn 17 where the displacement is a maximum. When ultrasonic horns are operated at high power levels, typically in excess of 10 W, the amplitude of the displacement of the tip may be several tens of microns. Operation of the ultrasonic horn at high power when the tip of the horn 17 is immersed in liquids at ambient pressure will give rise to acoustic cavitation in the liquid and the flow of liquid away from the tip by a phenomenon known as acoustic streaming. Acoustic cavitation in water at ambient pressure is achieved at a power density in excess of 0.5-1.0 W per square centimeter of horn tip and at a frequency of 20 kHz. In some embodiments of the present invention, the acoustic horn 15 may comprise a base end 25 that may provide a contact with the ultrasonic transducer 20 to provide for the ultrasonic transducer 20 to vibrate the acoustic horn 15.

The resonant frequency of the acoustic device operating in a longitudinal mode may be determined by the size of the ultrasonic transducer 20 and the acoustic horn 15 and the materials from which the ultrasonic transducer 20 and the acoustic horn 15 are constructed. The design of the acoustic horn 15 may vary and may be a stepwise tapering, a smooth tapering with an exponentially reducing diameter or the like. The acoustic horn 15 may be designed such that the tapering is degenerated to a single step giving the acoustic horn 15 a pin-like shape. Other horn shapes can be envisaged, including the case where its thickness is very much less than the wavelength of sound and the horn is a thin layer of material that is coupled to the ultrasonic transducer 20. In embodiments of the present invention, the design of the acoustic horn 15 may be such as to provide amplification of the acoustic energy onto the tip of the horn 17. In certain aspects of the present invention, the acoustic horn 15 may be made of titanium. Additionally, in certain aspects, the area of the horn tip 17 may be of the order of tenths of square centimeters. In some embodiments of the present invention, the length of the acoustic horn 15 may be an odd integer multiple N of half the wavelength ($\lambda/2$) of the acoustic wave generated by the ultrasonic transducer 20.

Figure 2A:
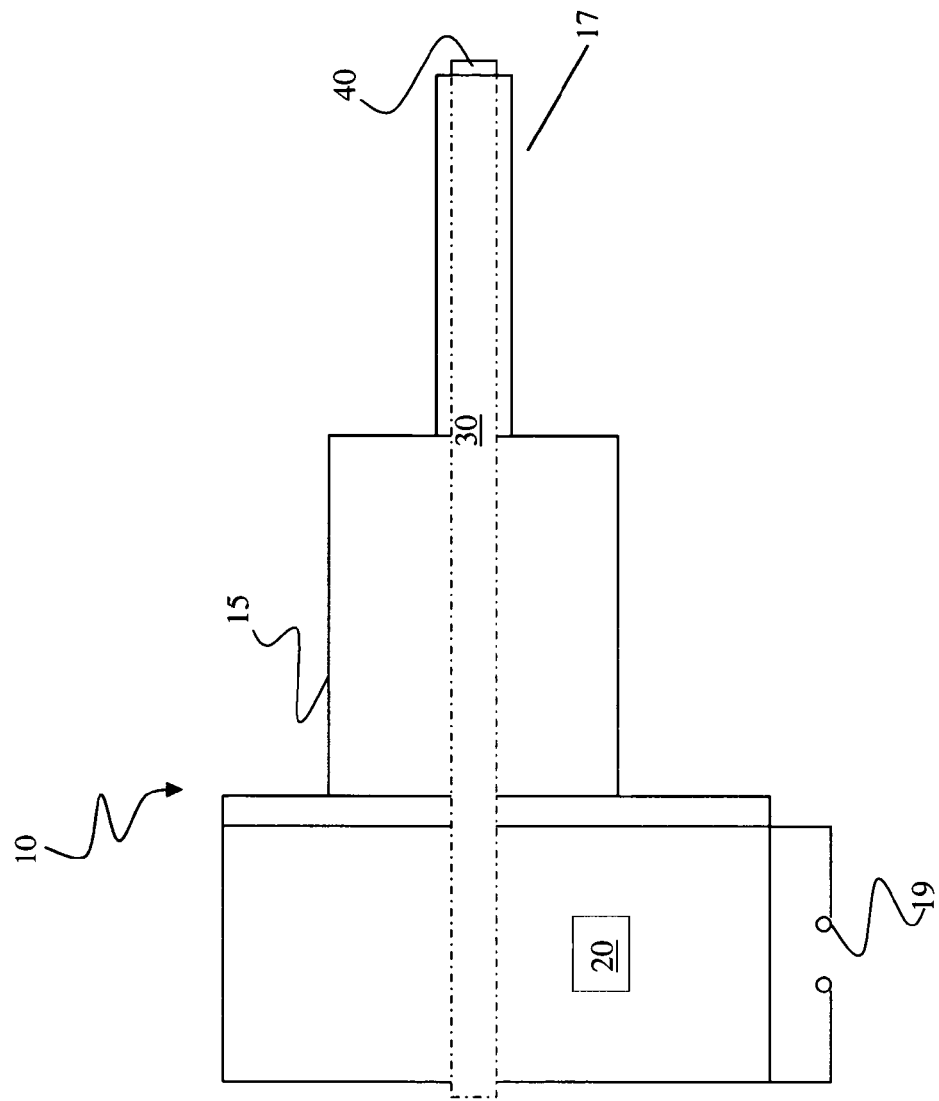
FIG. 2A is a schematic-type diagram showing a high power acoustic resonator with integrated optical interfacial element, in accordance with an embodiment of the present invention.

FIG. 2A is a schematic of a high power acoustic resonator with an integrated optical interfacial element, in accordance with an embodiment of the present invention. In accordance with embodiments of the present invention, an optical conduit 30 is integrated into the high power acoustic resonator 10. The optical conduit 30 may be a fiber optic, a light pipe coated on an interior surface with a highly reflective medium, such as gold, or the like. In the illustrated embodiment, the integrated optical interfacial element is an optical window 40 disposed at a tip of the acoustic horn 17.

The optical window 40 may be made of a hard, transmissive material such as diamond (natural or synthetic), sapphire or quartz that transmits the electromagnetic radiation being used with the high power acoustic resonator. In one aspect of an embodiment of the present invention, the optical interfacial element may be attached directly by means of any standard bonding methods such as brazing, soldering, gluing, compression bonding and/or the like. In a further aspect of an embodiment of the present invention, the optical interfacial element may comprise a single crystal diamond (a type II or similar purity diamond) and may be bonded into a metal holder (not shown) that is located in the tip of the acoustic horn. The metal holder into which the hard and transmissive material is bonded may comprise tungsten carbide or another material with a low thermal expansion coefficient to provide for the use of the high power acoustic resonator with integrated optical interfacial element and optical system in extreme temperature situations, such as down a hydrocarbon producing wellbore or in a material stream of a manufacturing process. The hard and transmissive material may be bonded to a metal holder by means of soldering using a copper/silver/titanium active braze or the like to provide for robustness of the system.

In certain aspects of the present invention, the metal holder containing the hard and transmissive material may be soldered to the tip of the acoustic horn 17 using a solder with a melting point below that of the solder used to bond the hard and transmissive material to the metal holder. Merely by way of example, such solders may comprise the eutectic alloys gold/germanium and copper/silver or the like. In some embodiments of the present invention, the acoustic horn 15 may be comprised of an inert metal with a low coefficient of thermal expansion, such as titanium or the like.

As depicted in FIG. 2A, embodiments of the present invention provide for the coupling of the optical conduit 30 with the acoustic horn 15. As described above, the acoustic horn 15 provides for transmitting the acoustic energy produced by the high power acoustic resonator 10 onto the tip of the acoustic horn 17. As such, by locating the optical window 40 at the tip of the acoustic horn 17 or proximal to the tip of the acoustic horn 17, embodiments of the present invention may provide for effective acoustic cleaning of the optical window 40. Moreover, in certain embodiments of the present invention wherein the high power acoustic resonator 10 may be used to acoustically determine properties of a substance located on the tip of the acoustic horn 17, the amplification of the acoustic energy onto the tip may increase the sensitivity/accuracy of the high power acoustic resonator 10 as a sensing device.

For optical interactions with a substance disposed on or proximal to the optical window 40, it is necessary in embodiments of the present invention, to provide optical access to the optical window 40. In embodiments of the present invention, this optical access is provided using the optical conduit 30. As discussed in more detail above, the acoustic horn 15 is a component with a design to provide for transmitting the acoustic energy of the high power acoustic resonator 10 onto the tip of the acoustic horn 17 and the optical window 40. Disposing of the optical conduit 30 within the acoustic horn may mean locating the optical conduit within an external volume defined by the peripheral surface of the optical horn 15. In some embodiments of the present invention, the acoustic horn 15 may comprise a plurality of elements and, in such embodiments, a volume defined by the outer surfaces of the plurality of elements may be used to contain the optical conduit and/or the optical conduit 30 may be disposed within one of the plurality of elements.

In some embodiments of the present invention, the optical conduit 30 may pass through the body of the acoustic horn 15 and through the ultrasonic transducer 20. In other embodiments of the present invention, the optical conduit 30 may pass through the body of the acoustic horn 15 and may not pass through the ultrasonic transducer 20. The radiation is transmitted into the horn using an optical conduit, such as a gold-coated light pipe or an optical fiber, passing through the acoustic horn and the attached piezoelectric elements. Metal (or metal-coated) light pipes have been used over many years to transmit mid- and far-infrared radiation, in which spectral regions it has been difficult to find materials that exhibit sufficiently low absorptivities to allow radiation to be transmitted over relatively short distances (order 1 meter). Gold-coated light pipes are available commercially from companies such as Epner Technology Inc. Optical fibers can also be used to transmit radiation to the internal reflection element. A quartz fiber can be used to transmit visible ($\lambda$=0.4-0.8 $\mu$m) and near-infrared ($\lambda$=0.8-2.0 $\mu$m) radiation over considerable distances (10 s of meters to kilometers). In contrast, transmission of mid-infrared radiation ($\lambda$=2.0-25 $\mu$m) through optical fibers is considerably more challenging and requires materials such as chalcogenide glasses and silver halides (chloride and bromide) to transmit the radiation over distances of the order of 1 meter. Silver halide fibers for transmitting mid-infrared radiation in the spectral range 4-16 $\mu$m are commercially available from CeramOptec.

In an embodiment of the present invention, an electromagnetic radiation source 33 may emit electromagnetic radiation down the optical conduit 30, through the optical window 40 and onto a substance to be analyzed and/or imaged. Merely by way of example, the electromagnetic radiation source 33 may be a laser or the like. In the embodiment depicted in FIG. 2A, a beam splitter 36 may be located at one end of the optical conduit 30 and may provide for directing electromagnetic radiation returning down the optical conduit 30 after interacting with the substance being analyzed onto an electromagnetic detector 39. In a basic embodiment of the present invention the radiation source 33 may be an illumination source and the electromagnetic detector 39 may be an eye. In other embodiments, the electromagnetic detector 39 may be a charged couple device, a complementary metal oxide semiconductor, a photodiode, photomultiplier, a photodiode array and/or the like. The electromagnetic detector 39 may be connected to a processor 45 that may process the information collected by the electromagnetic detector 39. Then processor 45 may be a computer, a software application, a signal processor or the like.

As depicted in FIG. 2A, the external environment may be imaged through the optical window 40 using the beam splitter 36 in the illumination path length or with no illumination source. Moreover, the entire illustrated system may be made steerable so as to be able to illuminate and/or image areas and/or substances of interest in the external environment.

As noted, in certain embodiments, no spectral analysis is performed, and instead the high powered acoustic resonator with optical interfacial elements may simply provide for illumination or observation of the sample or environment outside of the acoustic horn, where the role of the acoustic horn is to keep the optical interfacial element clean and capable of transmitting optical radiation for illumination or visualization. For example, long-term bio-film build up on simple windows in marine environments requires frequent cleaning, which can be difficult or costly in remote locations.

Figure 2B:
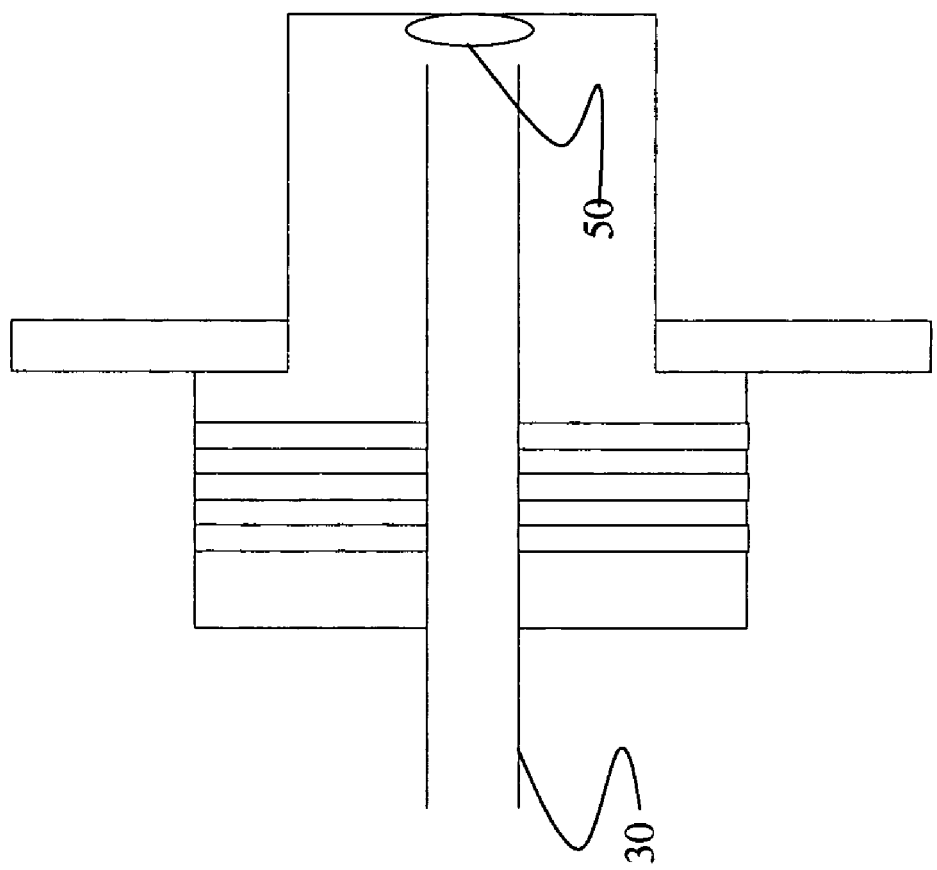
FIG. 2B is a schematic-type diagram illustrating a high power acoustic resonator with integrated optical interfacial element, including an integrated light pipe and a lens, in accordance with an embodiment of the present invention.

FIG. 2B illustrates a high power acoustic resonator with a lens as the integrated optical interfacial element and the optical system as an optical conduit, in accordance with an embodiment of the present invention. Such a design may be incorporated into a microscope where the lens 50 in the acoustic horn 15 may comprise the objective lens of the microscope.

Figure 3:
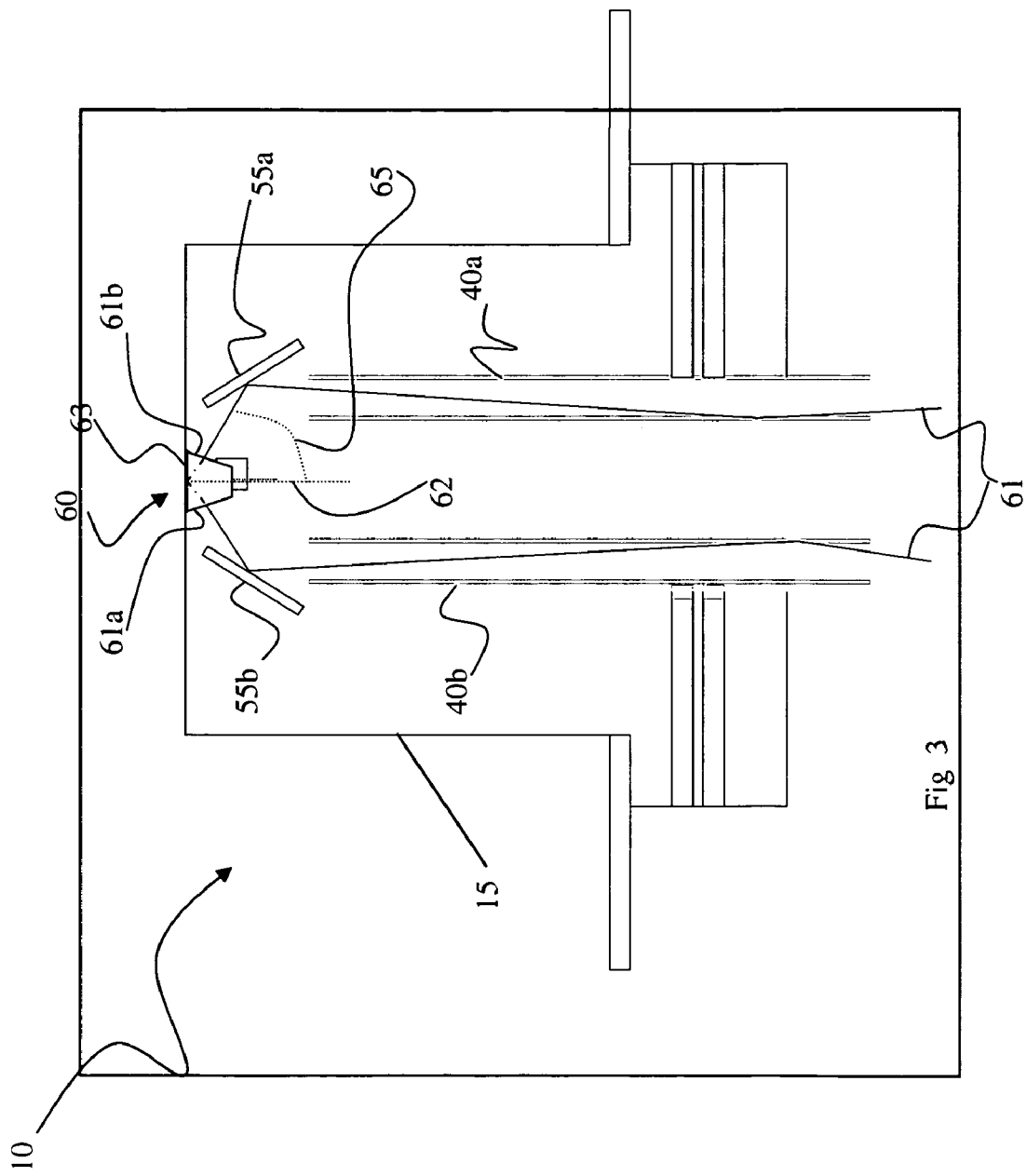
FIG. 3 is a schematic-type diagram illustrating a high power acoustic resonator with integrated optical interfacial element located in the tip of an acoustic horn and optical system, in accordance with an embodiment of the present invention.

FIG. 3 is a schematic that illustrates a high power acoustic resonator with an integrated optical interfacial element, which consists of a prism located in the tip of an acoustic horn, in accordance with an embodiment of the present invention. In the depicted embodiment, a prism 60 or the like, whose cross section may be substantially that of a truncated triangle, may be coupled with the acoustic horn 15. In certain aspects, sides of the prism 60 may be soldered to a metal holder (not shown) that holds the prism in place. The prism 60 may have an upper plane that may act as a total internal reflecting surface and may be in contact with the material to be analyzed.

The spectral characteristics of a material that is in contact with, or proximal to, an optical interfacial element can be collected by measuring the absorbance (or optical density) A as a function of the wavelength λ (or frequency ν) of the radiation passing through the material. The absorbance A is defined as $$A = -\ln\left(\frac{I}{I_o}\right) = \varepsilon C L$$

where $I_o$, is the intensity of the radiation passing through the optical system in the absence of the sample, I is the intensity of the radiation passing through the optical system and the material, ε is the absorption coefficient of a component in the material, C is the concentration of the component in the material and L the path length of the radiation in the material. The absorbance A as a function of λ or ν constitutes the spectral properties of the material. The spectral properties of the material can be used to both identify the presence of a component in the material and determine its concentration.

In embodiments of the invention as depicted in FIG. 3, electromagnetic radiation may be passed onto the prism 60 by means of the optical conduit 40b and passed back from the prism 60 into optical conduit 40a. The angle α of sloping faces 61a and 61b of the prism 60 with respect to the internal reflecting surface 63 of the prism 60 may be selected such that the angle α may be equal to an angle of internal reflection 65 with respect to the normal 62 of the internal reflection surface 63 when the incident beam 61 is normal to the face of the prism 63. The angle θ must be chosen to be greater than the critical angle of the material from which the prism 60 is made. The parallel beam of electromagnetic radiation 61 may be reflected onto the sloping face 61a of the prism 60 by planar reflector 55a that may comprise a highly reflective material, such as highly polished aluminum, gold or the like. After undergoing internal reflection at the internally reflecting surface 63 the parallel beam of electromagnetic radiation may pass through the sloping face 61b of the prism onto the planar reflector 55b and be reflected into the optical conduit 40a. An angle γ of the planar reflectors 55a and 55b with respect to the plane of the internally reflecting surface 63 may be such that planar reflectors 55a and 55b may direct the parallel beam of electromagnetic radiation 61 onto the sloping faces 61a and 61b of the prism 60 at an angle of 90° to provide that the reflected beam is normal to the face of the prism.

The angle γ is related to the angle α by $$\gamma = 90 - \frac{\alpha}{2}$$

noting that γ is also the angle of incidence of the parallel beam with respect to the plane of the reflector. The angular tolerances may be ±1° or more preferably ±0.5°. The electromagnetic radiation incident on the planar reflectors 55a and 55b may form, in certain aspects, a substantially parallel beam with a beam divergence of less than 3° or, in some aspects, less than 1.5°.

The depth of penetration $D_p$ of the totally internally reflected radiation is related to the angle of reflection θ at the window-sample interface by:

$$D_p = \frac{\lambda}{2\pi(n_1^2\sin^2\theta - n_2^2)^{1/2}}$$

where $n_1$ is the refractive index of the internal reflection element, $n_2$ is the refractive index of the sample ($n_1 > n_2$) and λ is a wavelength of the electromagnetic radiation. For example, when the prism 60 is made of diamond, the refractive index $n_1$ may be in the range of 2.50-2.35 for electromagnetic radiation with a wavelength in the range of 0.4-20 μm. The internal reflection angle θ and the prism angle α may be set to 45°, whereupon the angle of the planar reflectors 55a and 55b may be set to provide that γ=67.5°. In the case of the prism 60 comprising a diamond, the refractive index of the diamond prism ($n_1$=2.43) in contact with water ($n_2$=1.34) and with electromagnetic radiation of wavelength λ=3.0 μm incident on the diamond prism at an angle of incidence θ=45° may provide a depth of penetration of 0.44 μm. Moreover, the depth of penetration may decrease to about 0.34 μm when the substance in contact with the internal reflection surface 63 of the diamond prism is a low pressure gas, where $n_2$ very close to unity.

The electromagnetic radiation emitted from a source (not shown) in the depicted embodiments may be made substantially parallel by one of several means. For example, an optical system consisting of three lenses may be used to generate a collimated beam of electromagnetic radiation. Alternatively, a precision collimator for visible and near-infrared spectral measurements (λ=0.6-1.1 μm) consisting of two lenses, where each of which has two different radii of curvature, may also be used to create the collimated beam for the depicted embodiments. Further, a laser source may be used to produce a collimated electromagnetic radiation beam at a desired wavelength.

Figure 4:
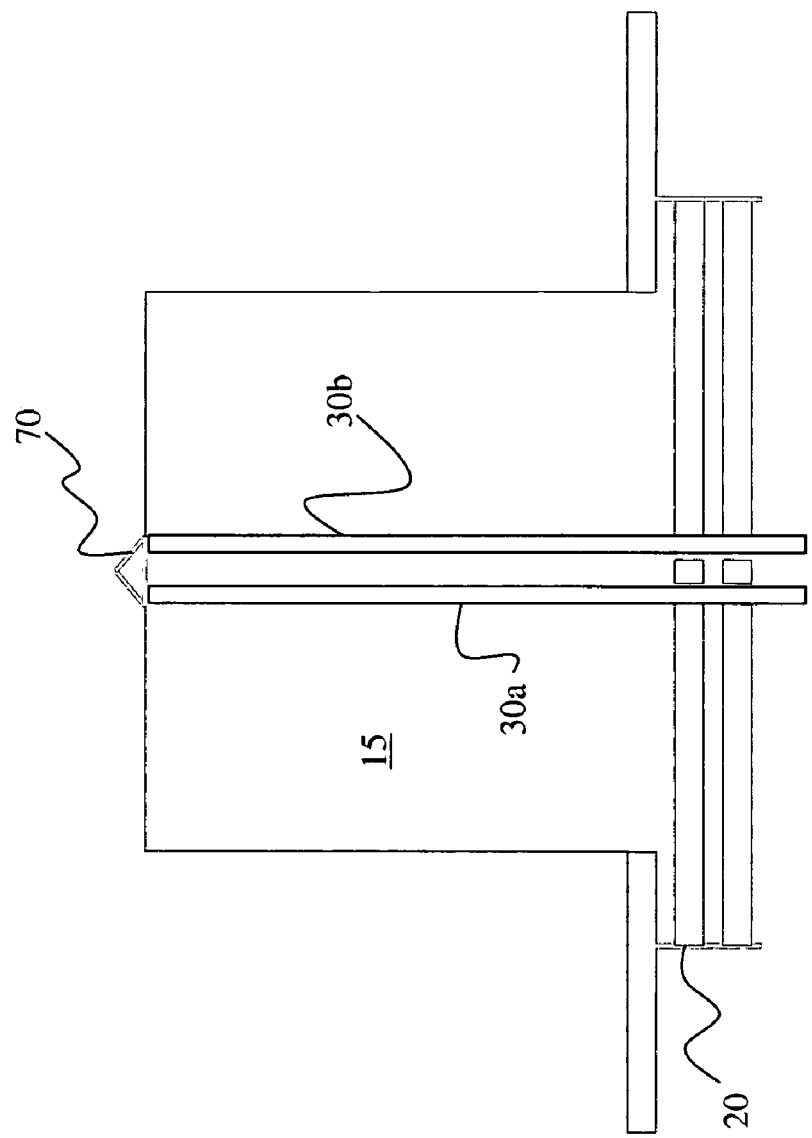
FIG. 4 shows a schematic of a prism incorporated into an acoustic horn, in accordance with an embodiment of the present invention.

FIG. 4 shows a schematic of a prismatic element incorporated into an acoustic horn, in accordance with the present invention. As depicted, a prismatic optical interfacial element 70 protrudes from the acoustic horn 15. The prismatic optical interfacial element 70 may have a cross section that may be shaped like a triangle, a truncated triangle or the like. The prismatic optical interfacial element 70 may be connected to a radiation source (not shown) and a detector (not shown) by means of the optical conduit 30a passing through the body of the acoustic horn 15. Largely parallel electromagnetic radiation emerges from the optical conduit 30a so that the electromagnetic radiation is normally incident on the base of the prismatic optical interfacial element 70 and may undergo total internal reflection at an angle θ (with respect to the normal of the sloping prism surface), which is equal to the angle α of the prism.

With a condition that θ=α=45°, an internally reflected beam of the electromagnetic radiation may pass through the crystal along a path that is parallel to the plane of the base of the prism and may undergo a second internal reflection in the prismatic optical interfacial element 70 and exit the prismatic optical interfacial element 70 through the base of the prism and into the optical conduit 30b. In such configurations, the electromagnetic radiation may penetrate a sample substance essentially in contact with the prismatic optical interfacial element 70 with two internal reflections and a total penetration depth $D_p$ of the electromagnetic radiation in the sample may be two times the penetration depth as determined from the refractive index of the sample and the prismatic optical interfacial element 70.

In the embodiment of the present invention depicted in FIG. 4, the location of the internal reflection within the prismatic optical interfacial element 70 may be separated from the plane of the tip of the acoustic horn 17, acoustic cleaning of the prismatic optical interfacial element 70 may effectively occur when the prismatic optical interfacial element 70 may be made with proportions significantly smaller that the wavelength of the ultrasonic waves generated in the acoustic horn 15. Merely by way of example, in certain aspects the prismatic optical interfacial element 70 may be a diamond, a top of the prismatic optical interfacial element 70 may be about 3 mm from the tip of the acoustic horn 17 and the acoustic horn 15 may comprises titanium and the acoustic horn 15 may be made to resonate at 50 kHz. In such aspects, the wavelength of the ultrasound in titanium may be of the order of 0.121 m and the wavelength of the ultrasound in the diamond internal reflection element may be in the range of about 0.364 m. Further, the amplitude of the ultrasound may be close to its maximum value along the length of the diamond prismatic optical interfacial element. As such, even though the diamond prismatic optical interfacial element protrudes from the acoustic horn it may be acoustically cleaned.

A distribution of acoustic cavitation generated by an ultrasonic horn may be visualized by chemiluminescence generated in an aqueous solution of luminol and sodium carbonate. In a test of the preceding theoretical analysis, chemiluminescence from luminol exposed to high power ultrasound generated by an ultrasonic horn operating at 20 kHz in a luminol/sodium carbonate solution in which the wavelength of the ultrasound is 0.075 m showed that intense acoustic cavitation extends over a distance considerably greater than 3 mm from the tip of the acoustic horn 15 and, as such, may establish, that the protruding internal reflection element 70 of the depicted embodiment is cleaned.

Figure 5:
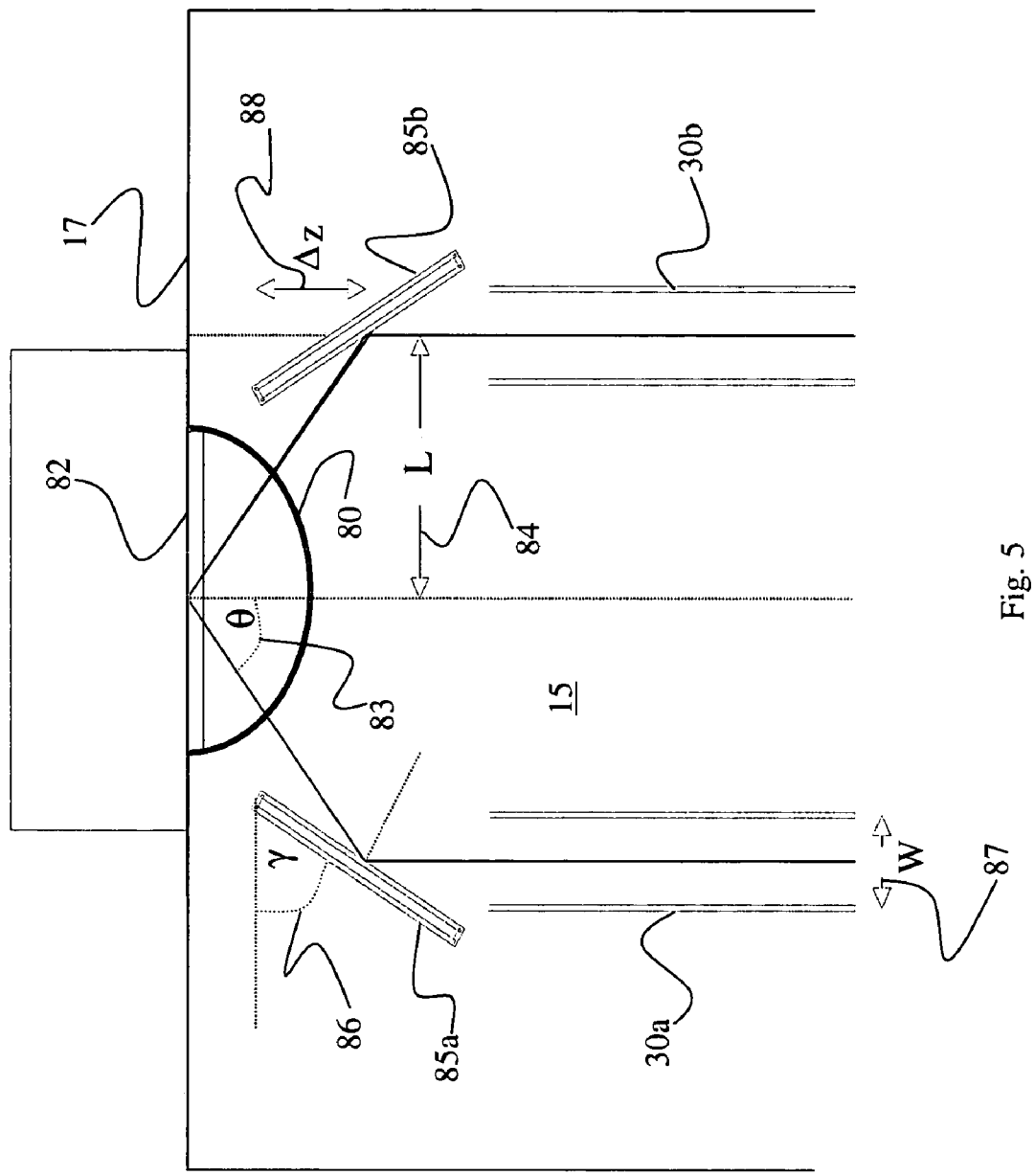
FIG. 5 is a schematic of a high power acoustic resonator with integrated optical interfacial element including moveable planar mirrors that may provide for varying an angle of incidence of electromagnetic radiation passing down an optical light pipe onto the optical interfacial element and configured so as to give rise to total internal reflection in the optical interfacial element located at a tip of an acoustic horn providing for reflection of electromagnetic radiation back down another optical light pipe, in accordance with an embodiment of the present invention.

FIG. 5 is a schematic of a high power acoustic resonator with integrated optical interfacial element and optical system including moveable planar mirrors that may provide for varying an angle of incidence of electromagnetic radiation passing down an optical conduit onto a total internal reflection element located at a tip of an acoustic horn, in accordance with an embodiment of the present invention. In the depicted embodiment, when the value of the refractive index $n_1$ of an internal reflection element 80 is significantly less than 2, as for example when the internal reflection element 80 consisting of sapphire having a refractive index $n_1$ equal to about 1.7, the critical angle $\theta_c$, which marks the onset of total internal reflection in the internal reflection element 80 may vary markedly with the refractive index $n_2$ of a substance to be analyzed (not shown) that is substantially in contact with the internal reflecting surface 82 of the totally internal reflecting element 80. Under these conditions, in an embodiment of the present invention, the value of the angle of internal reflection θ 83 may be varied by the movement of an adjustable mirror or the like. In the depicted embodiment, a moveable planar mirror 85, as depicted two of the moveable planar mirrors 85a and 85b are associated with two optical conduits 30a and 30b, may be moved in tandem to adjust the value of the angle of internal reflection θ 83 to provide that total internal reflection is achieved from the internal reflection surface 82 and the reflected optical beam is returned down the other optical conduit.

The internal reflection element 80 may be a prism or the like with different physical shapes and properties. In the depicted embodiment, the internal reflecting element 80 comprises a semicircular or truncated semicircular cross section. The internal reflecting element 80 may comprise a crystal or the like and the internal reflecting surface 82 may be the base of the hemisphere and may be located in the plane located at a tip of the acoustic horn 17.

Merely by way of explanation of an example of operation of the depicted embodiment, for normal incidence of electromagnetic radiation relative to the hemispherical surface of the internal reflection element 80, an angle γ 86 of the moveable planar mirror 85 with respect to the plane of the tip of the horn is related to the angle of internal reflection θ 83 by the following relationship:

$$\gamma = 90 - \frac{\theta}{2}$$

The angle of internal reflection θ 83 may be varied by varying simultaneously both the angle γ 86 and the position of the moveable planar mirror 85 on a vertical axis passing through the mirror. The variation of angle γ 86 with a vertical displacement Δz 88 may given θ83 by the following relationship:

$$\Delta z = L\left(\frac{1}{\tan(2\gamma_2)} - \frac{1}{\tan(2\gamma_1)}\right)$$

where $\gamma_1$ and $\gamma_2$ are angles of the moveable planar mirror 85 with respect to the vertical, corresponding to angles of incidence $\theta_1$ and $\theta_2$ ($\theta_2 > \theta_1$), and L 84 is a distance between the centre of the crystal and centre of the beam.

For electromagnetic radiation formed into a beam with a finite beam width W 87 that, in certain embodiments of the present invention may be passed down a plurality of the optical conduits 30a and 30b and may provide an angle of incidence at the plane 82 of internal reflection over a range θ±Δθ resulting in depths of penetration of the internally reflected radiation with Δθ given by $$\Delta\theta = i - r$$

where i is the angle of incidence made by the radiation on the hemispherical surface $$i = \sin^{-1}\left(\frac{W}{2R}\right)$$

r is the angle of refraction of the radiation on the hemispherical surface of the internal reflection element of refractive index $n_1$ $$r = \sin^{-1}\left(\frac{W}{2n_1 R}\right)$$

and R is the radius of curvature of the internal reflection element 80. For example, in the case of a beam of radiation emitted from an optical conduit 30a of internal diameter 2 mm incident on a hemispherical sapphire internal reflection element with refractive index $n_1$=1.70 and R=4 mm, the maximum angle of incidence is i=14.5°, the maximum angle of refraction r=8.5° and the range of the internal reflection angle is $\Delta\theta$=±6°.

Figure 6:
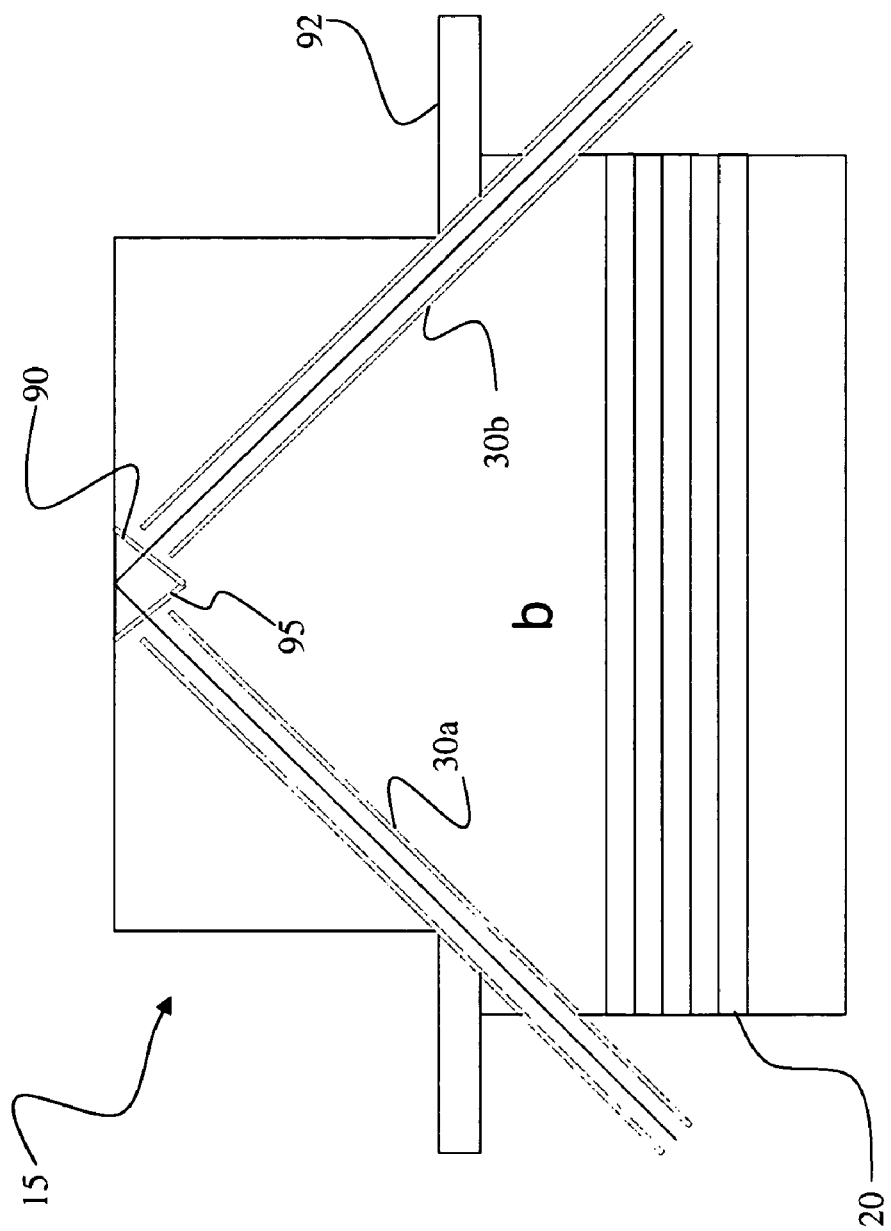
FIG. 6 is a schematic of an ultrasonic horn with an incorporated prism coupled with a pair of optical light fibers configured to pass through the horn, but not the ultrasonic transducer, in accordance with an embodiment of the present invention.

FIG. 6 is a schematic of an ultrasonic horn with an incorporated prism as the optical interfacial element coupled with a pair of optical conduits configured to pass through the horn, but not the ultrasonic transducer elements, in accordance with an embodiment of the present invention. In the depicted embodiment, two optical conduits 30a and 30b provide for passing electromagnetic radiation from a source (not shown) into and out of prism 90. The optical conduits 30a and 30b are integrated into an acoustic horn 15 but are angled within the acoustic horn so as not to pass through an ultrasonic transducer 20 configured to drive the acoustic horn 15.

The prism 90 may have a surface that may be positioned coincident with a plane located at a tip of acoustic horn 17. In some embodiments of the present invention, a sealing flange 92 may be used to couple the acoustic horn 15 with the acoustic conduits 30a and 30b and a structure supporting the ultrasonic transducer 20.

Merely by way of example, an angle β that each of the optical conduits 30a and 30b makes with the vertical may be equal to an angle of incidence θ of the electromagnetic radiation with the internal reflection prism 90. By adjusting the angle β and/or an angle α of the sloping faces of the prism 95, the electromagnetic radiation may be incident upon the sloping faces of the prism 95 with normal incidence. In such a way, the depicted embodiment may provide for optical measurements with regard to a substance substantially in contact with plane at the tip of the prism, where the electromagnetic radiation passes from and to optical conduits 30a and 30b located within the acoustic horn 15 that do not pass through the ultrasonic transducer 94.

Figure 7:
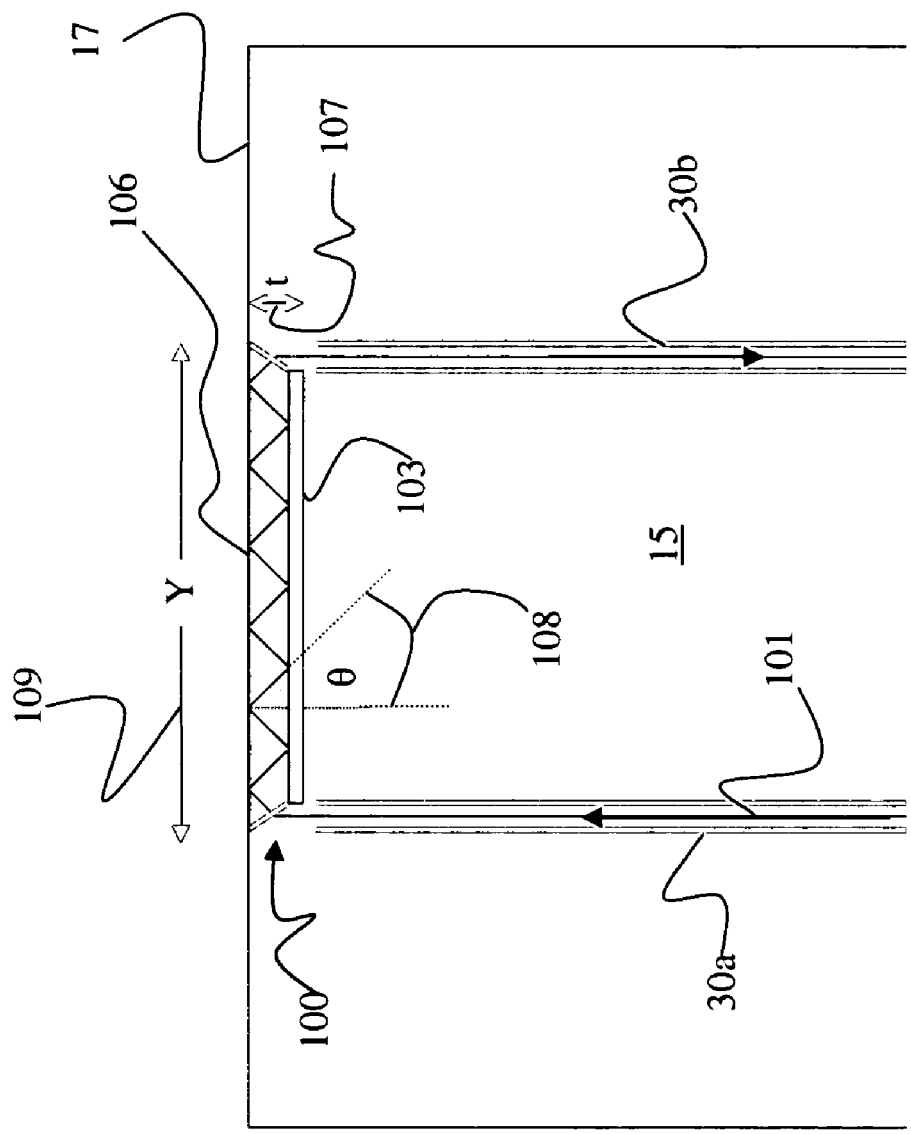
FIG. 7 illustrates an acoustic horn with integrated optical interfacial element and optical system where the optical interfacial element is a multibounce attenuated total reflection ("ATR") prism set at the tip of an acoustic horn and the optical system includes light pipes, in accordance with an embodiment of the present invention.

FIG. 7 illustrates an acoustic horn with integrated optical interfacial element and optical system including optical conduits and an integrated optical element configured to act as a multibounce ATR prism, the design of which is well known to those skilled in the art, substantially at a tip of the acoustic horn, in accordance with an embodiment of the present invention. In the depicted embodiment, a multibounce ATR element 100 may be located substantially at the tip of an acoustic horn 17. The multibounce ATR prism 100 may be coupled with two or more optical conduits. In the illustrated embodiment, the multibounce ATR prism 100 is coupled with two optical conduits 30a and 30b to provide for guiding of electromagnetic radiation into, through and out of the multibounce ATR prism 100. As with some of the other embodiments of the present invention discussed above, the multibounce ATR prism 100 may provide for electromagnetic radiation passing through the multibounce ATR prism 100 to interact with a substance substantially in contact with the multibounce ATR prism 100. In one embodiment of the present invention, the multibounce ATR prism 100 may be supported in its position in the acoustic horn by a support element 103. The support element 103 may be a non-absorbing, highly reflective base to provide for minimization of losses of electromagnetic radiation passing through the multibounce ATR prism 100.

In certain aspects, the multibounce ATR prism 100 may have proportions and reflection/transmission properties to provide for multiple reflections of an electromagnetic beam 101 that may pass down the optical conduit 30a, through the totally internally reflecting element 100 and then through the optical conduit 30b. Such a configuration may provide for multiple interactions of the electromagnetic beam 101 with a reflecting surface 106 of the multibounce ATR prism 100, wherein the reflection surface 106 may be in substantial contact with the substance to be detected/analyzed and may provide for detection/analysis of substances at low concentrations by increasing the optical path length of the electromagnetic radiation within the substance to be detected/analyzed by multiple values of the penetration depth $D_p$.

In some embodiments of the present invention, the internal reflecting element 100 may comprise diamond, sapphire or the like. Crystals such as diamond and sapphire may provide appropriate refractive indices and/or robustness for direct contact with substances to be detected/analyzed that may be located in extreme conditions or the like. The distance between internal reflections in the multibounce ATR prism 100 may be given by 2×t×tan θ, where the distance t 107 is the thickness of the multibounce ATR prism 100 and angle θ 108 is an angle of the internal reflection of the electromagnetic beam 101 in the multibounce ATR prism 100. Accordingly, a number of internal reflections of the electromagnetic beam 101 in the multibounce ATR prism 100 may be provided by the relationship Y/(2×t×tan θ), where length Y 109 is a length of the multibounce ATR prism 100. In such aspects, a total optical path length for the electromagnetic beam 101 in the multibounce ATR prism 100 may be provided by the relationship Y/sin θ, which is a relationship that is independent of the thickness of the multibounce ATR prism 100.

In certain embodiments, collection of spectra from samples may require optical path lengths considerably greater than the penetration depth of the electromagnetic radiation being used for the detection/analysis in total internal reflection mode. For example, for the detection of low concentrations of components in a gas or a clear (non-scattering) liquid an optical path length in the range 1 cm to 1 m may be required depending on the absorbance of the sample. In such circumstances, embodiments of the present invention comprising optical interfacial elements that transmit radiation may be in contact with the samples, and these transmission optical interfacial elements may be cleaned by the application of high power ultrasound through the acoustic horn.

Figure 8:
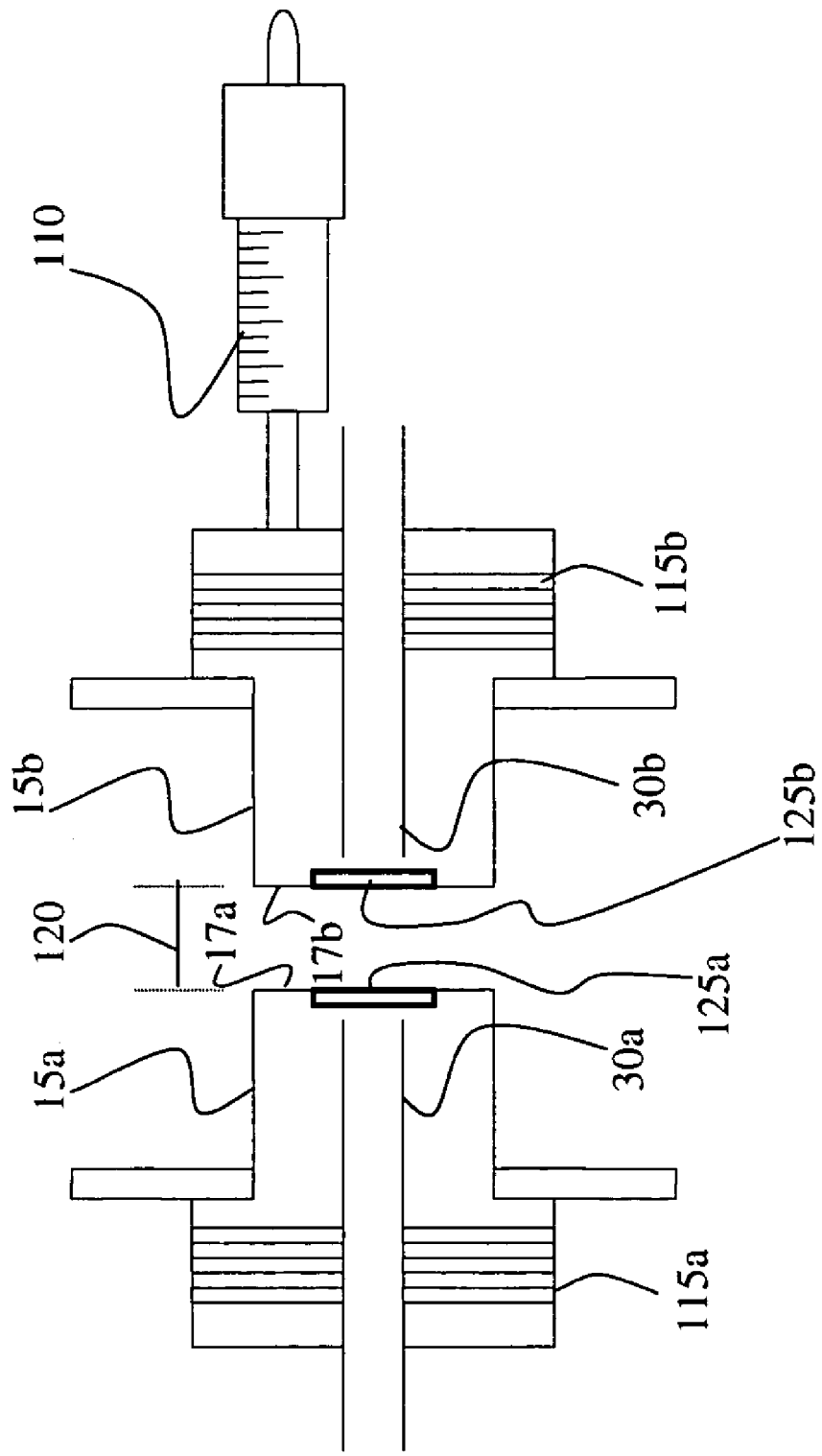
FIG. 8 shows a schematic of two acoustic horns with integrated optical interfacial elements and optical systems where the optical interfacial element is an optical window located at the tip of the acoustic horn and the optical system includes optical light pipes, in accordance with an embodiment of the present invention.

FIG. 8 shows a schematic of two acoustic horns with integrated optical windows, including optical conduits, located at the tip of the acoustic horn, in accordance with an embodiment of the present invention. In the depicted embodiment, an acoustic horn 15a has an optical window 125a disposed at around a tip of the acoustic horn 17a and another acoustic horn 15b has an optical window 125b disposed at or around a tip of the acoustic horn 17b. Ultrasonic transducers 20a and 20b may provide for propagation of acoustic energy through the acoustic horns 15a and 15b, respectively, and the acoustic horns 15a and 15b may transmit this acoustic energy to the tips of the acoustic horns 17a and 17b.

In certain aspects, the optical windows 125a and 125b may comprise a cylinder or the like of a crystal or the like that may be characterized by transmissivity in a spectral region of interest. Merely by way of example, crystals of diamond or sapphire may provide the required transmissivity in the spectral region comprising wavelengths in the range of 0.4-5 μm. In certain embodiments, a surface of each window 125a and 125b may contact a sample in a plane coincident with the tip of the acoustic horn, which may provide for acoustic cleaning of the optical window. In the depicted embodiment, the position of the acoustic horn 15a may be fixed while the acoustic horn 15b may be moveable along an axis joining the acoustic horn 15a and the acoustic horn 15b. In such an embodiment, an optical path length of the electromagnetic radiation passing between the optical windows 125a and 125b may be determined from a distance 120 between the tips of the two optical horns 15a and 15b. The distance 120 may be accurately varied using a micrometer 110.

In the depicted embodiment, the optical window 125a may be connected to an electromagnetic radiation source (not shown) by an optical conduit 30a. The optical window 125b may be connected to a radiation detector (not shown) by an optical conduit 30b, such as a light pipe or an optical fiber. The faces of the optical windows 125a and 125b may be coated with suitable anti-reflection coatings to minimize reflection losses. Such anti-reflection coatings are known in the art and single wavelength anti-reflection coatings may be composed of material with a thickness of $\lambda/4$—where $\lambda$ is a wavelength of electromagnetic radiation generated by the electromagnetic radiation source—and a refractive index $n_3 = \sqrt{(n_o \times n_1)}$—where $n_o$ is the refractive index of the medium through which the electromagnetic radiation is propagated immediately prior to incidence with the optical window of refractive index $n_1$. In the case of the optical conduit 30a being a light pipe, the medium is air and $n_o \approx 1$, whereupon $n_3 \approx \sqrt{n_1}$. For example, when the optical interfacial element is made of sapphire with $n_1 = 1.70$, the anti-reflective film may be characterized by $n_3 = 1.30$. A quarter wavelength coating of magnesium fluoride, characterized by $n_3 = 1.38-1.30$ in the wavelength range 0.5-5 μm may provide efficient anti-reflective properties to the sapphire optical interfacial elements. Wideband anti-reflection coatings may be prepared using multilayer coatings of various refractive indices. Both narrow and broadband anti-reflective coatings are commercially available. Lambda Research Optics Inc., for example, manufacture broadband anti-reflective coating in both the near- and mid-infrared spectral regions. The anti-reflective coating IEBAR (trademark) on zinc selenide gives a reflectance of less than 5% over the wavelength range 2.5-13 μm, while the coating BBAR-1250 (trademark) gives a reflectance of less than 1% over the wavelength range 0.95-1.6 μm.

Figure 9:
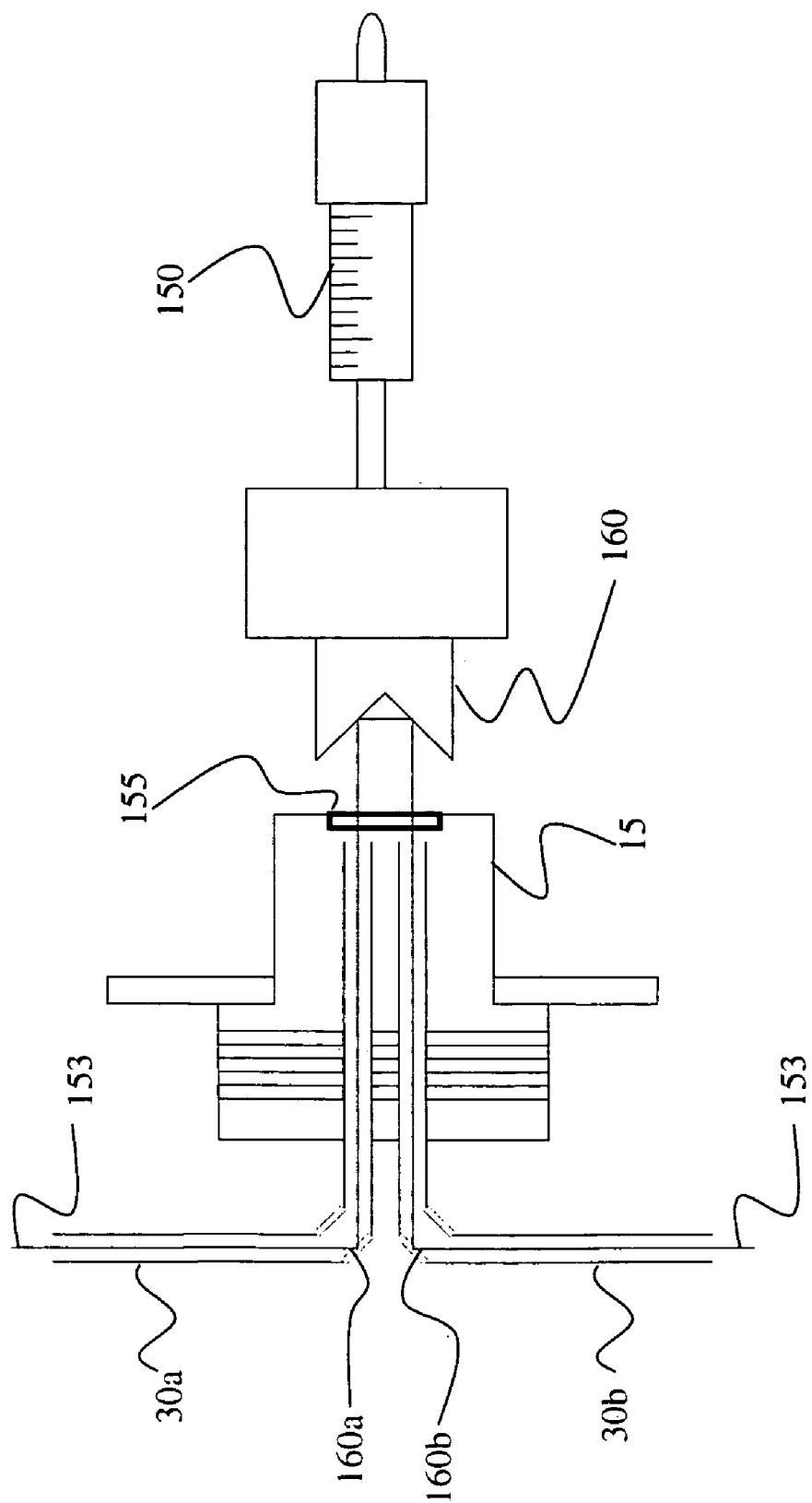
FIG. 9 depicts an acoustic horn incorporating an optical window disposed on the acoustic horn to provide an interface between an optical device and a sample in the plane of the tip of the horn, the optical system including a reflection element located outside the acoustic horn, in accordance with an embodiment of the present invention.

FIG. 9 depicts an acoustic horn incorporating an optical window disposed on the acoustic horn to provide an interface between the optical system and a sample in the plane of the tip of the horn and a reflection element located outside the acoustic horn, in accordance with an embodiment of the present invention. Certain embodiments of the present invention may provide for using a single optical window 155 and a combination of transmission and reflection of an electromagnetic radiation beam 153.

In the depicted embodiment, an optical conduit 30a may be used to propagate the electromagnetic radiation beam 153 through the acoustic horn 15 to the optical window 155 and then through a sample in contact with or located proximal to the optical window 155. After passing through the sample, electromagnetic radiation beam 153 may be reflected back through the sample by means of a reflecting surface 160 that may be a highly polished gold film or the like. The reflected electromagnetic radiation beam 153 may pass back through the optical window 155, through a second optical conduit 30b to a detector (not shown). In certain embodiments, a position of the reflecting surface 160 may be adjusted to control an optical path length of the electromagnetic radiation beam 153 through the sample. In an embodiment of the present invention, the reflecting surface 160 may itself be located on a tip of a second ultrasonic horn for purposes of acoustic cleaning.

In one embodiment, a substantially parallel beam of electromagnetic radiation, the electromagnetic radiation beam 153, may be propagated through the optical conduit 30a via a reflector 160a, which may be a planar mirror or the like, through the acoustic horn 15, out through the optical window 155 into the sample and is then reflected back through the sample by two reflecting surfaces, oriented at 45° with respect to the plane of the optical axis, and through the optical conduit 30b via a reflector 160b. The path length of the substantially parallel beam of radiation may be adjusted by moving the reflecting surface 160 that may be affected by micrometer 150.

Figure 10:
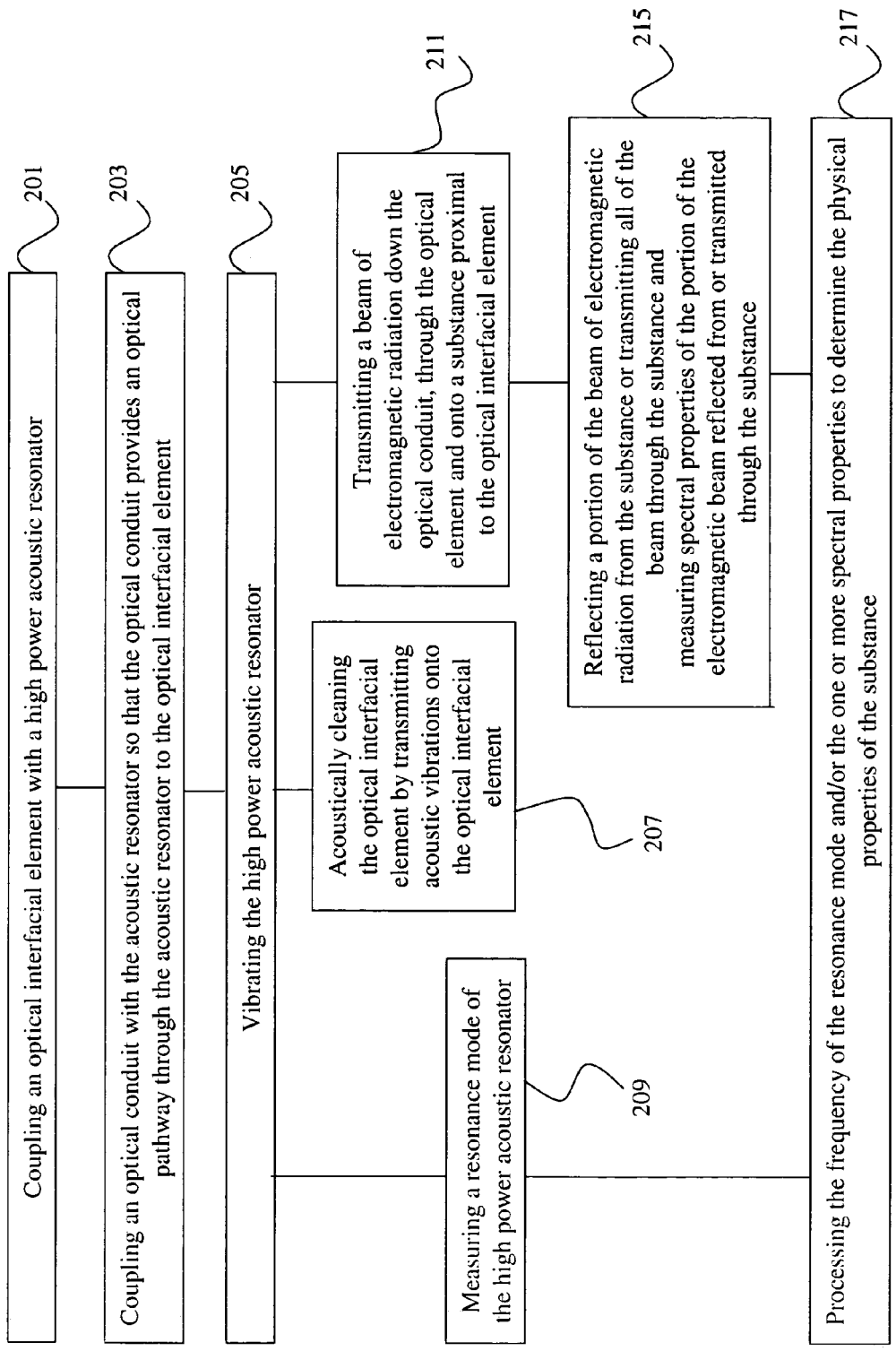
FIG. 10 is a flow-type diagram of a method for combining a high energy acoustic resonator with an optical interfacial element to provide for acoustic cleaning of the optical interfacial element, measuring a resonance mode of the acoustic resonator when contacted with a substance and/or measuring spectral properties of electromagnetic radiation interfacing with the substance, in accordance with an embodiment of the present invention.

FIG. 10 provides a flow-type diagram of a method for combining a high energy acoustic resonator with an optical interfacial element to provide for acoustic cleaning of the optical interfacial element, measuring a resonance mode of the acoustic resonator when contacted with a substance and/or measuring spectral properties of electromagnetic radiation interfacing with the substance, in accordance with an embodiment of the present invention. As depicted, in step 201, an optical interfacial element may be coupled with a high power acoustic resonator. In one embodiment of the present invention, the high power acoustic resonator may comprise an acoustic horn and an optical interfacial element may be positioned at a tip of the acoustic horn, in a plane defined by the tip of the acoustic horn and/or the like.

In step 203, one or more optical conduits may be coupled with the acoustic resonator to provide an optical pathway through the acoustic resonator to the optical interfacial element. The one or more optical pathways may be used to apply electromagnetic radiation to a substance proximal to the optical interfacial element or to return electromagnetic radiation that has interacted with the substance. In certain embodiments of the present invention, the one or more optical pathways may be disposed within the acoustic resonator to provide for a robust and self-contained system, minimize any adverse interactions between the acoustic and optic components and/or the like. Merely by way of example, the one or more optical conduits may be symmetrically disposed within the acoustic resonator.

In step 205, the high power acoustic resonator may be acoustically vibrated. In one aspect, in step 207, the acoustic vibration of the high power acoustic resonator may cause the optical interfacial element to vibrate and may provide for acoustic cleaning of the optical interfacial element. In another aspect, in step 209 a resonant mode of the high power acoustic resonator may be determined. In yet another aspect, in step 211, a beam of electromagnetic radiation may be transmitted through the optical interfacial element and onto a substance in contact with and/or proximal to the optical interfacial element. In step 215, spectral properties of a portion of the electromagnetic beam that has been reflected from and/or transmitted through the substance may be measured. In certain aspects, the portion of the electromagnetic beam travels through an optical conduit in the acoustic resonator to a spectral measurement device or the like. In step 217, output from the spectral measurement device and/or the measurement of the acoustic resonance mode may be processed by a processor, software or the like to determine physical properties of the substance.

In the foregoing description, for the purposes of illustration, various methods and/or procedures were described in a particular order. It should be appreciated that in alternate embodiments, the methods and/or procedures may be performed in an order different from that described. It should also be appreciated that the methods described above may be performed by hardware components and/or may be embodied in sequences of machine-executable instructions, which may be used to cause a machine, such as a general-purpose or special-purpose processor or logic circuits programmed with the instructions, to perform the methods.

Hence, while detailed descriptions of one or more embodiments of the invention have been given above, various alternatives, modifications, and equivalents will be apparent to those skilled in the art without varying the invention. Moreover, except where clearly inappropriate or otherwise expressly noted, it should be assumed that the features, devices and/or components of different embodiments may be substituted and/or combined. Thus, the above description should not be taken as limiting the scope of the invention, which is defined by the appended claims.

What is claimed is:

1. An optical interfacial device with combined optical and acoustical elements configured to provide for analyzing a material located at or near an optical interfacial element, comprising:
a high power acoustic resonator, wherein the high power acoustic resonator comprises:
an acoustic body having a first end and a second end, wherein the first end comprises a base and the second end defines a surface with an opening in said defined surface;
a transducer coupled with the first end and configured to vibrate the acoustic body, wherein the acoustic body is configured to transmit acoustic energy produced by the high power acoustic resonator onto the surface defined by the second end;
an optical system disposed within the high power acoustic resonator and configured to provide an optical path or paths from the first end to the opening in the surface defined by the second end; and
the optical interfacial element coupled with the second end of the acoustic body and disposed to provide for transmission of electromagnetic radiation into or out of the optical system through said optical interfacial element, wherein the optical interfacial element is further configured to seal the opening from an external environment, and wherein the optical interfacial element is configured to provide an external interface for optically analyzing the material.

2. The system of claim 1, wherein the optical interfacial element is configured to contact a material to be optically analyzed.

3. The system of claim 1, wherein the optical element is disposed at or proximal to the surface defined by the second end of the acoustic body.

4. The system of claim 1, wherein the second end of the acoustic body is located at a position such that the second end of the acoustic body experiences an antinode during vibration of the high power acoustic resonator.

5. The system of claim 1, wherein the optical system comprises an optical fiber.

6. The system of claim 1, wherein the optical system comprises a light pipe.

7. The system of claim 1, further comprising:
moveable mirrors configured to direct electromagnetic radiation onto and back from the optical interfacial element.

8. The system of claim 1, wherein the optical interfacial element comprises a prism.

9. The system of claim 1, wherein the optical interfacial element comprises a window.

10. The system of claim 1, wherein the optical interfacial element comprises a refractive or diffractive lens.

11. The system of claim 1, wherein the prism is shaped as one of a cone, and a truncated cone.

12. The system of claim 8, wherein the prism has a cross-sectional shape of one of a triangle, a truncated triangle, a semicircle, and a long thin rectangle.

13. The system of claim 1, wherein the optical interfacial element is configured to provide for formation of a totally internally reflecting surface when in contact with the material to be analyzed, wherein the electromagnetic radiation is reflected from the totally internally reflecting surface.

14. The system of claim 1, wherein the acoustic body comprises an acoustic horn.

15. The system of claim 14, wherein the optical interfacial element is disposed at a distance less than or equal to $\lambda/5$ from the surface defined by the second end of the acoustic body, and wherein $\lambda$, is wavelength of an acoustic wave in the acoustic horn.

16. The system of claim 1, wherein a resonant frequency of the high power acoustic resonator is in the range of 10 kHz to 250 kHz.

17. The system of claim 1, wherein the acoustic body is configured to transmit acoustic energy onto the sensing surface to provide for exertion of a physical force onto a substance located or deposited on the external interface.

18. The system of claim 1, wherein the optical interfacial element comprises one of natural diamond, synthetic diamond, sapphire, silica, silicon, germanium, zinc selenide, zinc sulphide, barium fluoride, calcium fluoride and yttrium oxide.

19. The system of claim 1, wherein the acoustic body comprises titanium.

20. The system of claim 1, wherein the acoustic body comprises stainless steel.

21. The system of claim 1, wherein the transducer comprises a piezoelectric element.

22. The system of claim 1, further comprising:
an electromagnetic radiation source coupled with the optical system; and
an electromagnetic radiation detector coupled with the optical system.

23. The system of claim 22, wherein the electromagnetic radiation source is configured to emit electromagnetic radiation with a wavelength in a region of between 2 and 25 µm.

24. The system of claim 22, wherein the electromagnetic radiation source comprises a laser.

25. The system of claim 22, further comprising:
a processor coupled with the high power acoustic resonator, the electromagnetic radiation source and the electromagnetic radiation detector and configured to control the high power acoustic resonator, the electromagnetic radiation source and the electromagnetic radiation detector and to receive measurements from the high power acoustic resonator, the electromagnetic radiation source and the electromagnetic radiation detector.

26. The system of claim 25, wherein the processor is configured to process a resonant frequency of the high power acoustic resonator and an amount of electromagnetic radiation detected by the electromagnetic radiation detector.

27. The system of claim 1, wherein the optical system passes through the transducer.

28. The system of claim 1, wherein the optical interfacial device with combined optical and acoustical elements is configured to function at temperatures in excess of 200 degrees Centigrade.

29. The system of claim 1, wherein the optical interfacial device with combined optical and acoustical elements is configured to function in fluid pressures exceeding 700 bar.

30. The system of claim 1, wherein the optical interfacial device with combined optical and acoustical elements is configured for use in a borehole penetrating an earth formation.

* * * * *